(12) United States Patent
Chamberland et al.

(10) Patent No.: US 10,792,322 B2
(45) Date of Patent: Oct. 6, 2020

(54) HERBAL COMPOSITIONS AND METHODS FOR THE PREVENTION AND TREATMENT OF PLANT OF NAIL INFECTIONS

(71) Applicant: MONDIAS NATURELS INC., Longueuil, Quebec (CA)

(72) Inventors: Guy Chamberland, Boucherville (CA); William Lee, Boucherville (CA)

(73) Assignee: MONDIAS NATURAL PRODUCTS INC, Longueuil (CA)

(*) Notice: Subject to any disclaimer, the term of this patent is extended or adjusted under 35 U.S.C. 154(b) by 0 days.

(21) Appl. No.: 16/076,352

(22) PCT Filed: Feb. 8, 2017

(86) PCT No.: PCT/CA2017/050142
§ 371 (c)(1),
(2) Date: Aug. 8, 2018

(87) PCT Pub. No.: WO2017/136930
PCT Pub. Date: Aug. 17, 2017

(65) Prior Publication Data
US 2019/0038696 A1      Feb. 7, 2019

Related U.S. Application Data

(60) Provisional application No. 62/292,608, filed on Feb. 8, 2016, provisional application No. 62/293,479, filed on Feb. 10, 2016, provisional application No. 62/293,519, filed on Feb. 10, 2016.

(51) Int. Cl.
| | | |
|---|---|---|
| A61K 36/00 | (2006.01) |
| A61K 36/66 | (2006.01) |
| A01N 65/06 | (2009.01) |
| A61K 36/14 | (2006.01) |
| A61K 36/53 | (2006.01) |
| A61K 36/61 | (2006.01) |
| A01N 65/28 | (2009.01) |
| A61K 9/00 | (2006.01) |
| A61K 47/26 | (2006.01) |
| A61K 9/70 | (2006.01) |
| A01N 31/08 | (2006.01) |
| A61K 36/185 | (2006.01) |
| A01N 65/08 | (2009.01) |
| A01N 65/00 | (2009.01) |
| A61P 31/04 | (2006.01) |
| A61P 31/10 | (2006.01) |
| A61K 45/06 | (2006.01) |

(52) U.S. Cl.
CPC .............. *A61K 36/66* (2013.01); *A01N 31/08* (2013.01); *A01N 65/00* (2013.01); *A01N 65/06* (2013.01); *A01N 65/08* (2013.01); *A01N 65/28* (2013.01); *A61K 9/0014* (2013.01); *A61K 9/7015* (2013.01); *A61K 36/14* (2013.01); *A61K 36/185* (2013.01); *A61K 36/53* (2013.01); *A61K 36/61* (2013.01); *A61K 47/26* (2013.01); *A61P 31/04* (2018.01); *A61P 31/10* (2018.01); *A61K 45/06* (2013.01); *A61K 2300/00* (2013.01)

(58) Field of Classification Search
None
See application file for complete search history.

(56) References Cited

U.S. PATENT DOCUMENTS

2006/0228428 A1     10/2006   Kang
2008/0106610 A1      5/2008   Kim

FOREIGN PATENT DOCUMENTS

| CN | 1141137 C | * 3/2004 |
| KR | 2006109063 A | * 10/2006 |
| KR | 20080041007 | 5/2008 |

OTHER PUBLICATIONS

Sunila et al, A preliminary study on antimetastatic activity of *Thuja occidentalis* L. in mice model. Immunopharmacology and Immunotoxicology, (Jul. 1, 2006) vol. 28, No. 2, pp. 269-280 (Year: 2006).*
Extended European Search Report dated Aug. 1, 2019 in corresponding patent application EP17749858.1.
Biswas, R. et al.; "Thujone-Rich Fraction of Thuja occidentalis Demonstrates Major Anti-Cancer Potentials: Evidences from In Vitro Studies on A375 Cells", Hindawi Publishing Corporation, vol. 2011, Article ID 568148, 16 pages; Accepted Apr. 9, 2010.
Krahulcova, A.; "Cytotaxonomic Study of *Chelidonium majus* L. s. 1", Springer, Folia Geobotanica & Phytotaxonomica, vol. 17, No. 3 (1982), pp. 237-268.
Zielinska, S. et al.; "Greater Celandine's Ups and Downs—21 Centuries of medicinal uses if Chelidonium majus From the Viewpoint of Today's Pharmacology", Frontiers in Pharmacology, Apr. 2018, vol. 9, Article 299, 29 pages.

* cited by examiner

*Primary Examiner* — Qiuwen Mi
(74) *Attorney, Agent, or Firm* — Robert Brouillette (57) ABSTRACT

It is disclosed a pharmaceutical and/or phytosanitary composition comprising an aqueous extract of *Chelidonium majus* root and an acceptable pharmaceutical or phytosanitary excipient, for the prevention or treatment of plant infections and/or for the prevention or treatment of nail 5 infections. The composition may further comprise an aqueous extract of *Thuja occidentalis* leaf; and from about 1 to 5% of at least one natural phenolic compound. The composition is efficient in the treatment of plant infection (mildew fungus, blight fungus, etc); the treatment of intumescence of a plant; the treatment of potatoes (powdery or common scab, *Rhizoctonia*, etc), and also allows a higher crop yield: without the use of a chemical fungicide. The composition also allows rapid treatment of fungus infection of nails.

23 Claims, 9 Drawing Sheets

FIGURE 1A: Infected tomato plant    FIGURE 1B: Infected tomato plant

FIGURE 1C: Tomato plant after several weeks and one single application

FIGURE 3A: Infected plant           FIGURE 3B: Treated plant

FIGURE 4A: Infected plants (Day 0)

FIGURE 4B: Infected plants – Spread stopped (Day 1)

FIGURE 4C: Infected plants – Spread stopped (Day 2)

Day 0: infected plant

Day 1: White spots are browning

Day 0: infected plant

Day 1: White spots are browning

Cured plant

Untreated group     CELEXT07 treated group

Scab infection

From severe (top), light (middle) and light (bottom)

Rhizoctonia infection

From severe (top), light (middle) and light (bottom)

FIGURE 9

HERBAL COMPOSITIONS AND METHODS FOR THE PREVENTION AND TREATMENT OF PLANT OF NAIL INFECTIONS

CROSS-REFERENCE TO RELATED APPLICATIONS

The present patent application claims the benefits of priority of commonly assigned U.S. Patent Applications No. 62/292,608 entitled "Compositions And Methods For Treatment Of Nail Fungal Or Bacterial Infections" and filed at the U.S.P.T.O. on Feb. 8, 2016; No. 62/293,479 entitled "Herbal Phytosanitary Compositions And Methods For The Prevention And Treatment Of Plant Infections" and filed at the U.S.P.T.O. on Feb. 10, 2016; and No. 62/293,519 entitled "Herbal compositions for treatment of nail and skin infections" and filed at the U.S.P.T.O. on Feb. 10, 2016; the content of which is incorporated herein by reference.

FIELD OF THE INVENTION

The present invention generally relates to phytosanitary and/or pharmaceutical compositions and methods for the prevention and/or treatment of plant infections or nail infections. In particular, the phytosanitary and/or pharmaceutical compositions are herbal compositions.

BACKGROUND OF THE INVENTION

Plant Infection Treatments:

The plant cuticle is composed of three distinct substances (i.e., waxes, cutin, and pectin) that typically act as barriers against the entry of many compounds into plant tissues. Certain chemical adjuvants (such as penetration enhancing components) can directly modify leaf waxes and increase film tension of the leaf surface in order to enhance cuticular permeability. Foliar spray of adjuvants onto plants has been associated with effective fungicidal activity.

Aqueous type pesticides have a short history. The pesticide water solubility was overcome by the 1970s and water is now used as a carrier. Previous pesticide formulations were not formulated to use water as their carrier. The waxy surfaces of many insects, fungi, and plants make it difficult for most water-based spray solutions to penetrate their target. To overcome this barrier, adjuvants were developed. Adjuvants are ingredients added to a spray tank to enhance the pesticide's activity, such as surfactants, spreader stickers, crop oils, antifoaming materials, buffering agents, and compatibility agents.

Surfactants are adjuvants that facilitate and accentuate the emulsifying, dispersing, spreading, wetting, or other surface modifying properties of liquids. It is recognized that without an adjuvant, 30-50% reduction in efficacy occurs.

Several types of formulations exist to try to deliver the active agents across the cuticle:

Microemulsions of pesticides are a formulation that decrease the use of organic solvents and increase the wettability, dispersibility, and penetration ability of the pesticide droplets. Microemulsion is defined as a colloidal dispersion composed of oil phase, aqueous phase, surfactant and co-surfactant at appropriate ratios.

Nanoemulsions are also used for delivering chemical compounds across the cuticle. The efficacy of this approach is based on the small size of nanoemulsion droplets, the large surface area of the emulsion, the low surface tension of the entire system, and the low interfacial tension of the droplets.

Surfactants are adjuvants that reduce surface tension within the external surface layers of water. There are four different types of surfactants but only anionic and non-ionic surfactants are commonly used in pesticides formulations. Anionic Surfactants are negatively charged, and enhance foaming and other spreading properties whereas Nonionic Surfactants do not have a charge in solution and are used to break water surface tension. Cationic Surfactants are positively charged and are not used as they can disrupt membrane ion balance and cause injury to the plant. Amphoteric Surfactants, depending upon the pH of the solution, will form either a positive or negative charge in water. These are rarely used.

Penetrants dissolve or penetrate waxy layers on leaves and allow other chemicals to interface with plant cells or insect epidermal tissue and enter the spaces between the epidermal cells, sometimes called "cell free space." Penetrants can contain petroleum by-products, crop oils, complex alcohols, and other hydrocarbon-based materials.

Thickeners can be used to reduce drift of sprays. They may consist of polyacrylamide, polyethylene polymers, polysaccharides (long-chain sugars), or vegetable oils. These products not only help volatile pesticides become less volatile, they also cause the carrier solution to become more viscous and heavier.

Emulsifier agents work by coating tiny particles or groups of the liquid molecules and preventing them from coagulating with other like molecules. The emulsifiers allow oil and water solutions to mix. These products are usually added by the manufacturer and are commonly mixed with petroleum-based pesticides to help them mix more readily with water.

Spreader and Stickers. Spreaders are compounds allowing the surface tension of the pesticide to be reduced in such a way that it easily spreads into a very thin film over a surface. Like surfactants, spreaders and stickers increase the efficiency of the pesticide dramatically. They may consist of fatty acids, latex, aliphatic alcohols, crop oils such as cottonseed, or inorganic oils. Stickers are very much like thickening agents or oils in that they cause the pesticide solution to adhere to the leaf surface, resisting rain, evaporation and runoff.

Oils. There are two types of oil: crop oils that are derived from soybean and other crops, and inorganic oils that come from petroleum refineries. Some are used as suffocates, which cover the insect and cut of its air supply. Others are used as penetrants to break apart the chitin layers (such as with scales) and cause the insect to die. Still others are used like surfactants, forming film over the leaf, breaking down the cuticle, and allowing the pesticide to enter its target. Some oils are blended with surfactants, to take advantage of the properties of both adjuvants.

Alkyl polyglucosides are modified sugar molecules that have surfactant-like properties and can be used as spreader/stickers.

Organosilicate surfactants are very good at increasing the "rainfastness" of pesticides. They also reduce the surface tension and allow everything from micronutrients to fungicides to enter the leaf stomates.

There is a need for a new phytosanitary compositions for treating plant infections allowing a better penetration in the plant to treat the infection while minimizing or avoiding the use of chemical pesticides that can be damageable for the environment.

Nail Infections:

The conventional approach used is to design formulations that will penetrate through the nail plate to deliver the antifungal or antibacterial agent to the site of infection. Conventional treatments are administered for 6 to 12 months to patients but fail because the fungus or its spores remain 'hidden' within the nail tissue including the nail root.

Alternative medicine practitioners may treat fungal or bacterial infections of the nails using thymol dissolved in alcohol. This formulation is applied once or twice daily to the affected area. Other plant-based formulations includes the use of creams or ointments or tinctures (alcoholic) containing Tea tree oil and or thymol.

For the treatment of onychomycosis, penetration of the topical antifungal agent through the nail plate from the surface of the nail and diffusion of the antifungal drug through the nail bed is the basis of the past and current medical treatment. Oral administration of antifungal agents is rarely used because of the systemic toxicity of the antifungal drugs and the dose levels required to achieve effective dosages at the site of infection. The medical practice may include the combination of an antifungal with topical urea; where the urea is used to degrade protein (keratin protein is part of the composition/structure of the nail) and enhance the penetration of the antifungal agent.

The medical literature defines onychomycosis as a progressive fungal infection of the nails and if left untreated may cause destruction and deformity of the nail. It is primarily caused by dermatophytes, particularly *Trichophyton rubrum* and *Trichophyton mentagrophytes* (Ghannoum M. A. et al., J Am Acad Dermatol 2000; Vol. 43, Number 3: 641-648). Today, both oral drugs (e.g. terbinafine and itraconazole) and topical drugs (e.g. ciclopirox, amorolfine, efinaconazole, and tavaborole) are available for the treatment of fungal nail infection. Unfortunately, these agents can cause systemic toxicity, such as liver toxicity, as well as cause drug-drug interactions. The efficacy of topical formulations has been demonstrated in clinical trials to be relatively low and this poor efficacy is associated to poor nail penetration/permeability and high binding to keratin protein. Additionally, the recently approved topical drugs efinaconazole and tavaborole have low efficacy and local side effects issues. According to current scientific state of the art (see Tabata Y. et al., Antimicrob Agents Chemother. 2015 Dec. 7; 60(2):1035-9), in order to be effective against onychomycosis, a topical antifungal should have low molecular weight and low affinity to keratin protein. The low molecular weight is considered an important factor for penetration of the nail.

Traditional and modern scientific art has only resulted in very low efficacy against what is clinical defined as mild-to-moderate onychomycosis despite the use of relatively small molecules to attempt to penetrate through the nail plate. Scientists have used methods such as applying urea (as part of the formulation) to limit binding to the keratin in the nail and hence increase penetration. Other formulations, such as Penlac™, use a lacquer formulation to help increase penetration. Other methods include grinding the nail surface to increase penetration. Unfortunately, both old and modern pharmaceutical and natural agents (such as thymol and tea tree oil) have failed to significantly treat mild-to-moderate nail infections and completely failed to treat severe nail infections. For instance, recently approved drug Jublia™ boasts a 17% efficacy (versus 3% for placebo) in mild-to-moderate onychomycosis and there is no approved drug or natural agent for the treatment of severe infections.

There is a need for a new pharmaceutical compositions for treating nail or skin infections allowing a better nail or skin penetration while minimizing or avoiding side effects.

It has been discovered that the same herbal composition can be useful for treating either plant infections or for treating nail infections.

SUMMARY OF THE INVENTION

The shortcomings of the prior art are generally mitigated by highly effective compositions for the prevention or treatment of foliar or root fungal and bacterial infections; or for the treatment of nail infections as disclosed herein.

The invention is first directed to a pharmaceutical and/or phytosanitary composition comprising an aqueous extract of *Chelidonium majus* root and an acceptable pharmaceutical or phytosanitary excipient, for the prevention or treatment of plant infections and/or for the prevention or treatment of nail infections.

According to a preferred embodiment, the composition may further comprise from about 1 to 5% of at least one natural phenolic compound. Preferably, the at least one natural phenolic compound may comprise phenolic acids, thymol, carvacrol, eugenol, crassinervic acid, aduncumene, hostmaniane, gaudichaudanic acid, flavonoids, tannins, stilbenes, curcuminois, coumarins, ligans, quinines, or mixture thereof.

According to a preferred embodiment, the composition may further comprise an aqueous extract of *Thuja occidentalis* leaf.

According to a preferred embodiment, the composition may further comprise a film-forming surfactant, such as but not limited to film-forming surfactant comprising a polysorbate-type nonioninc surfactant.

According to a preferred embodiment, the composition may further comprise additives selected form the group consisting of penetrants, thickeners, emulsifiers, spreader, stickers, crop oils, inorganic oils, alkyl polyglucosides, and organosilicate surfactants.

According to a preferred embodiment, the composition may further comprise an antifungal compound. Preferably, the antifungal compound is selected from the group consisting of amphotericin B, terbinafine, tavaborole, ciclopirox, griseofulvin, an azole antifungal, an echinocandins, and flucytosine. More preferably, the azole antifungal is ketoconazole, fluconazole, itraconazole, posaconazole, voriconazole, or efinaconazole; and the echinocandin is anidulafungin, caspofungin, or micafungin.

According to a preferred embodiment, the composition may further comprise an antibacterial compound. Preferably, the antibacterial compound comprises beta-lactam antibiotics, macrolide antibiotics, lincosamides, streptogramins, aminoglycosides, quinolones, sulfonamides, tetracyclines, chloramphenicol, metronidazole, tinidazole, nitrofurantoin, glycopeptides, lipoglycopeptides, oxazolidinones, rifamycins, polypetides and tuberactinomycins or mixtures thereof.

According to a preferred embodiment, the aqueous extract of *Chelidonium majus* root is a 10:1 ethanol-water extract of the *Chelidonium majus* root, with 10 being the amount of *Chelidonium majus* root and 1 being the amount of ethanol-water.

The invention is also directed to a phytosanitary composition for treating plant infection, comprising:
from 0.2 to 1 wt. % of *Chelidonium majus* root extract;
from 0 to 1 wt. % of *Thuja occidentalis* leaf extract;
from 0 to 0.5 wt. % of Thymol;
from 0 to 0.5 wt. % of Carvacrol; and
from 0 to 0.25 wt. % of film-forming surfactant.

The invention is also directed to a pharmaceutical composition for treating nail infection, comprising:
from 40 to 50 wt. % of *Chelidonium majus* root extract;
from 40 to 50 wt. % of *Thuja occidentalis* leaf extract;
from 0 to 5 wt. % of *Eucalyptus citriodora*, essential oil;
from 0 to 4 wt. % of Tea tree oil;
from 0 to 1 wt. % of *Thymus vulgaris* flower-leaf; and
from 0 to 10 wt. % of film-forming surfactant.

According to a preferred embodiment, the pharmaceutical composition may comprise:
about 44.6 wt. % of *Chelidonium majus* root extract;
about 44.6 wt. % of *Thuja occidentalis* leaf extract;
about 1.8 wt. % of *Eucalyptus citriodora*, essential oil;
about 2.7 wt. % of Tea tree oil;
about 0.9 wt. % of *Thymus vulgaris* flower-leaf
about 5.36 wt. % of Polysorbate 20.

The invention is also directed to the use se of a pharmaceutical or phytosanitary composition as defined herein, for the prevention or treatment of plant infection or for the prevention or treatment of nail infection.

The invention is also directed to a method for the prevention and treatment of plant bacterial and fungus infections, comprising the step of applying at least once, a composition as defined herein on the plant.

The invention is also directed a method for the prevention and treatment of nail infections, comprising the steps of:
applying at least one time, a composition as defined herein on a nail to be treated; and
letting the composition to dry such as to form a film on the nail.

The present invention is a highly effective phytosanitary or pharmaceutical composition for the prevention or treatment of fungal and bacterial infections on plants or nails.

Preferably, the phytosanitary composition is used for foliar applications such as on leaves, stems, branches, twigs, buds and/or flowers of the plant to be treated.

In accordance with a preferred embodiment, the composition may comprise an aqueous extract of *Chelidonium majus* root.

In accordance with a preferred embodiment, the composition may comprise an aqueous extract of *Chelidonium majus* root combined with *Thuja occidentalis* leaf.

In accordance with a preferred embodiment, the composition may comprise an aqueous extract of *Chelidonium majus* root:
with or without *Thuja occidentalis* leaf;
with or without from about 1 to 5% natural phenolic compounds;
with or without a film-forming surfactant; and/or
with or without at least one of the following ingredients: penetrants, thickeners, emulsifiers, spreader, stickers, crop oils, inorganic oils, alkyl polyglucosides, and/or organosilicate surfactants.

It is also disclosed a method for phytosanitary treatment of plants, the method comprising at least the steps of applying once or several times the composition as defined herein on the plants. Preferably, the composition is applied on leaves, stems, branches, twigs, buds and/or flowers of the plant to be treated.

It is also disclosed the use of the composition as defined herein for phytosanitary treatment of plants. For instance, the composition is particularly useful for treating mildew. Other infections can also be treated.

Natural phenolic compounds found in essential oils may be used to avoid the oil-base to damage the plant.

Natural phenolic compounds are defined as low molecular weight naturally occurring organic compounds which contains one or more phenolic group. They are naturally produced by plants. These include: phenolic acids, thymol, carvacrol, eugenol, crassinervic acid, aduncumene, hostmaniane, gaudichaudanic acid, flavonoids, tannins, stilbenes, curcuminois, coumarins, ligans, quinines, etc.

The composition is particularly efficient in the treatment of plant infection (mildew fungus, blight fungus, etc); the treatment of intumescence of a plant; the treatment of potatoes (powdery or common scab, *Rhizoctonia*, etc), and also allows a higher crop yield: without the use of a chemical fungicide.

The composition is also particularly efficient in the treatment of fungus infection of nails.

Other and further aspects and advantages of the present invention will be obvious upon an understanding of the illustrative embodiments about to be described or will be indicated in the appended claims, and various advantages not referred to herein will occur to one skilled in the art upon employment of the invention in practice.

BRIEF DESCRIPTION OF THE DRAWINGS

The above and other aspects, features and advantages of the invention will become more readily apparent from the following description, reference being made to the accompanying drawings in which.

DETAILED DESCRIPTION OF PREFERRED EMBODIMENTS

A novel pharmaceutical and/or phytosanitary composition will be described hereinafter. Although the invention is described in terms of specific illustrative embodiments, it is to be understood that the embodiments described herein are by way of example only and that the scope of the invention is not intended to be limited thereby.

As used herein % or wt. % means weight % unless otherwise indicated. When used herein % refers to weight % as compared to the total weight percent of the phase or composition that is being discussed.

By "about", it is meant that the value of weight %, time, or temperature can vary within a certain range depending on the margin of error of the method or device used to evaluate such weight %, time, or temperature. A margin of error of 10% is generally accepted.

The pharmaceutical and/or phytosanitary composition (hereafter named "the composition") as disclosed herein comprises an aqueous extract of *Chelidonium majus* root and an acceptable pharmaceutical and/or phytosanitary excipient or base. According to a preferred embodiment, the aqueous extract of *Chelidonium majus* root is a 10:1 ethanol-water extract of the *Chelidonium majus* root, with 10 being the amount of *Chelidonium majus* root and 1 being the amount of ethanol-water.

The composition as disclosed herein may further comprise *Thuja occidentalis* leaf.

The composition as disclosed herein may further comprise from about 1 to 5% of natural phenolic compounds. Natural phenolic compounds found in essential oils may be used to obtain a synergistic response while avoiding the oil-base that will damage the plant. Natural phenolic compounds are defined as low molecular weight naturally occurring organic compounds which contains one or more phenolic group. They are naturally produced by plants. These include, but are not limited to: phenolic acids, thymol, carvacrol, eugenol, crassinervic acid, aduncumene, hostmaniane, gaudichaudanic acid, flavonoids, tannins, stilbenes, curcuminois, coumarins, ligans, quinines, etc.

The composition as disclosed herein may further comprise a film-forming surfactant.

The composition as disclosed herein may further comprise several additives such as, but not limited to penetrants, thickeners, emulsifiers, spreader and stickers, crop oils and inorganic oils, alkyl polyglucosides, and/or organosilicate surfactants.

Treatment of Plant Infections
Dormant Bud Foliar Application:

Depending on the agricultural/horticultural use, the composition or formulation may contain essential oils instead of the natural phenolic compounds. In these cases, the standardized (standardized to the natural phenolic compound) essential oils replace the natural phenolic compounds normally found within the oil; for example, *Thymus vulgaris* flower-leaf essential oil replaces the thymol compound. The switch to the standardized essential oil is to provide a better coating (film-formation) of the dormant bud. The standardized essential oil may contain an equivalent amount of the phenolic compound.

Soil (with or without Fertilizer) Application Formulations:

It is also disclosed a highly effective root (soil application) composition for the prevention or treatment of fungal and bacterial infections, comprising an aqueous extract of *Chelidonium majus* root with or without *Thuja occidentalis* leaf with or without from about 1 to 5% natural phenolic compounds with or without fertilizer ingredients with or without film-forming surfactant, penetrants, thickeners, emulsifiers, spreader and stickers, crop oils and inorganic oils, alkyl polyglucosides, and/or organosilicate surfactants.

This invention is based on the synergistic activity between aqueous herb extracts and the natural phenolic compounds obtained from plants. Natural phenolic compounds found in essential oils are used to obtain the synergistic response while avoiding the oil-base that will damage the plant.

Natural phenolic compounds are defined as low molecular weight naturally occurring organic compounds which contains one or more phenolic group. They are naturally produced by plants. These include: phenolic acids, thymol, carvacrol, eugenol, crassinervic acid, aduncumene, hostmaniane, gaudichaudanic acid, flavonoids, tannins, stilbenes, curcuminois, coumarins, ligans, quinines, etc.

It is also disclosed a method for the phytosanitary treatment of plants, comprising the step of applying a phytosanitary composition as defined herein on the plants, such as on the roots of the plants, or on the leaf, the stem, the branch, the twig, the bud and/or the flower.

As demonstrating with the following examples, efficacy of the treatment can be seen after one day and only one single application of the formulation.

The following composition in accordance with a preferred embodiment of the invention has been tested on plants.

Formulation Used for Infected Plants:

TABLE 1

General composition of the composition for treating plants

| Ingredients: | wt. % |
|---|---|
| *Chelidonium majus* root extract | 0.2-1% |
| *Thuja occidentalis* leaf extract | 0-1% |
| thymol | 0-0.5% |
| carvacrol | 0-0.5% |
| Surfactant (Polysorbate 20) | 0% or 0.25% |

TABLE 2

Specific compositions for treating plants

| Ingredients | Foliar application - active infection (wt. %) | Soil drench - active infection (wt. %) | Foliar prevention (wt. %) | Soil drench prevention (wt. %) |
|---|---|---|---|---|
| *Chelidonium majus* 10:1 root extract | 1% | 1% | 0.2-0.5% | 0.2-0.5% |
| *Thuja occidentalis* leaf extract | 0-1% | 0.5-1% | 0% | 0% |
| thymol | 0.1-0.5% | 0.1-0.5% | 0% | 0% |
| carvacrol | 0.1-0.5% | 0.1-0.5% | 0% | 0% |
| Fertilizer | None | Optional | Optional | optional |
| Surfactant (Polysorbate 20) | 0.25% | 0% | 0.25% | 0% |

Method of Making: 1000 mL Preparation of Agricultural Formula

Step 1:

Thuya extract: 260 gram foliage dried macerated in 3 times its volume in water for 72 hours; filtered and solution retained.

Step 2:

Add *Chelidonium majus* extract (CELEXT07) according to table xx to 900 mL water in the spray tank or drench container and mix to dissolve the extract powder.

Step 3:

Add Thuya extract, thymol, carvacrol and or surfactant to container of Step 2 according to table XX. QS to 1000 mL.

Example 1: Foliar Spray of Tomato Plants Infected with Blight Fungus

*Passalora fulva* (*Cladosporium fulvum*) causes tomato leaf mould. Foliage is often the only part of the plant infected and causes infected leaves to wither and die, indirectly affecting yield. In severe cases, blossoms and fruit can also be infected directly reducing yield.

Treatment of infected tomato plants has been done on Day 1, 3 and 5 with foliar spray comprising an aqueous 1:10 (1 part root to 10 parts water) extract of *Chelidonium majus* root with 0.25% of a surfactant such as polysorbate 20.

Figure 1A:
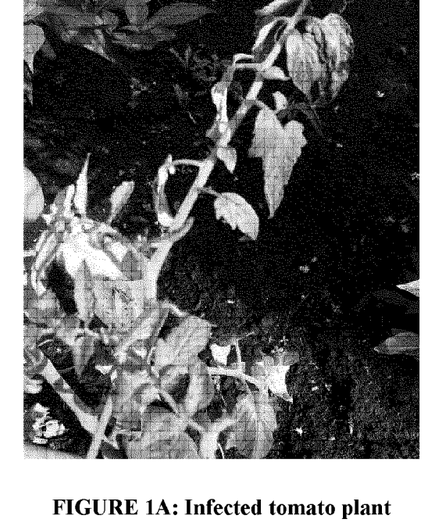
FIGS. 1A, 1B and 1C are pictures of tomato plants infected by blight fungus before treatment (FIGS. 1A and 1B) and after several weeks of treatment (FIG. 1C), with a composition in accordance with a preferred embodiment.
Figure 1B:
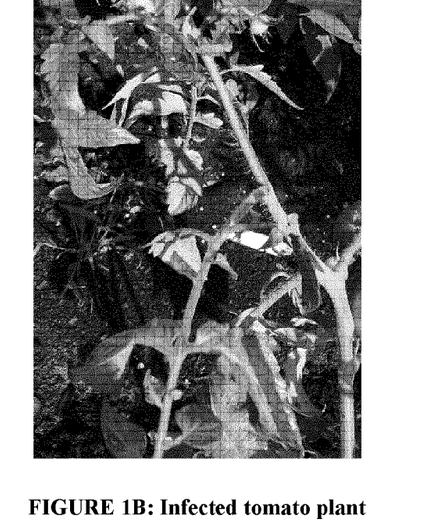
Figure 1C:
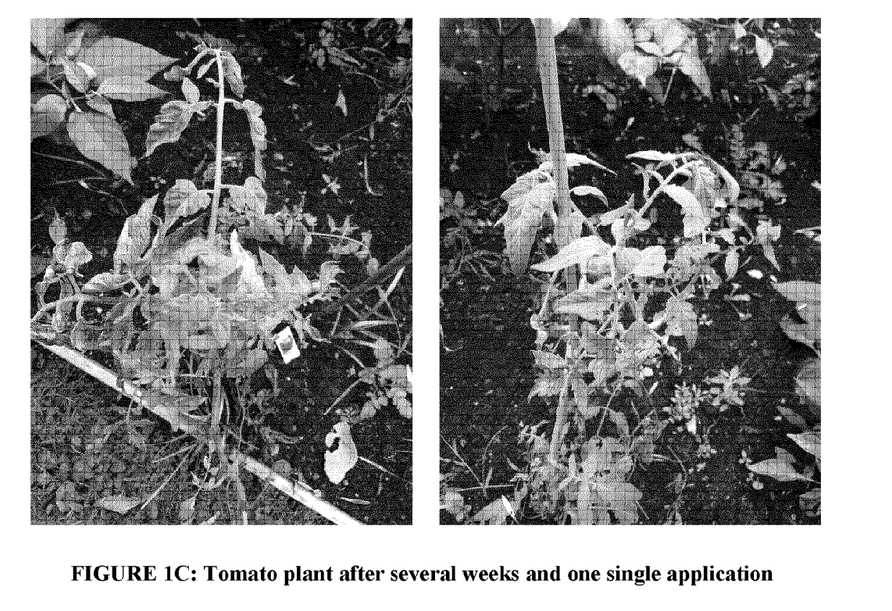

As shown by comparing the pictures presented in FIGS. 1A and 1B and in FIG. 1C, single foliar application to tomato plants shows effective recovery from infection after several days and one single application. Field study demonstrated that the infection did not spread to adjacent uninfected plants and that growth was evidence post-treatment in the affected plants.

Example 2: Foliar Spray of Tomato Plants Infected with Powdery Mildew

Figure 2A:
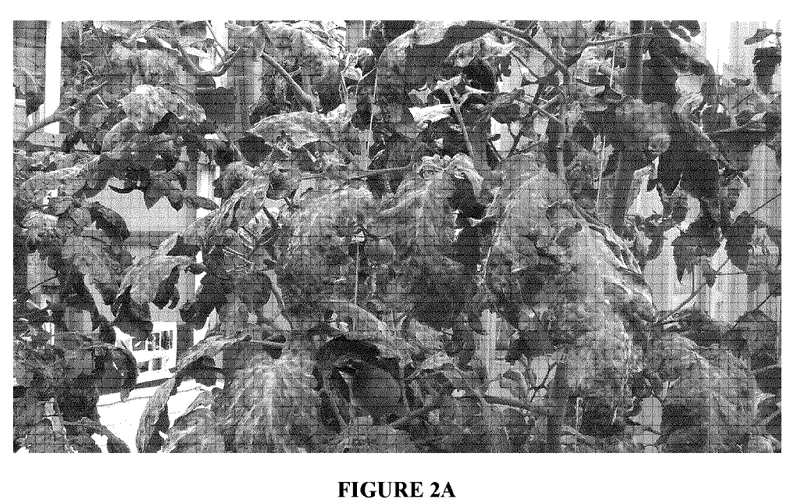
FIGS. 2A and 2B re pictures of tomato plants infected by powdery mildew before treatment (FIG. 2A) and after several weeks of treatment (FIG. 2B), with a composition in accordance with a preferred embodiment.

Powdery mildew is a disease of leaf tissue (see FIG. 2A). Yield and fruit quality are reduced because the disease develops quickly, and severely affected leaves are killed. This results in less fruit being produced.

Figure 2B:
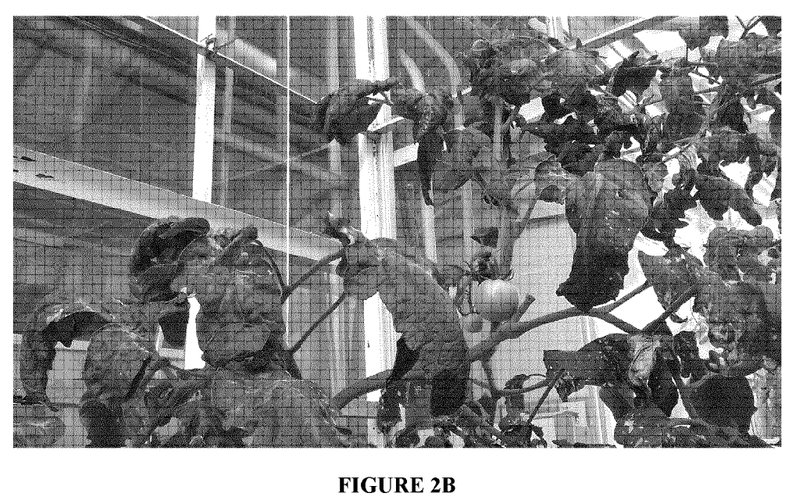

Treatment of infected tomato plants has been done on Day 1 and 3 with foliar spray comprising 1% of an aqueous 10:1 (10 part root to 1 parts water-ethanol) extract of *Chelidonium majus* root, 1% thymol with 0.25% of a surfactant such as polysorbate 20. Two sprays to end-of-season hydroponic tomato plants, heavily infected with powdery mildew, resulted in significant improvement in comparison to unsprayed plants (See FIG. 2B). Spore load was clearly reduced on all leaves, and cleared from young leaves. The latter is particularly important since plants were able to continue to grow to support late-season fruit load.

Example 3: Treatments of Cucurbits Infected with Mildew Fungus

Figure 3A:
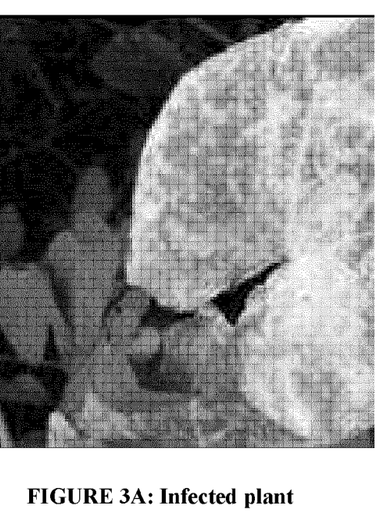
FIGS. 3A and 3B are pictures of cucurbits plants before treatment (FIG. 3A) and after treatment (FIG. 3B), with a composition in accordance with another preferred embodiment.
Figure 3B:
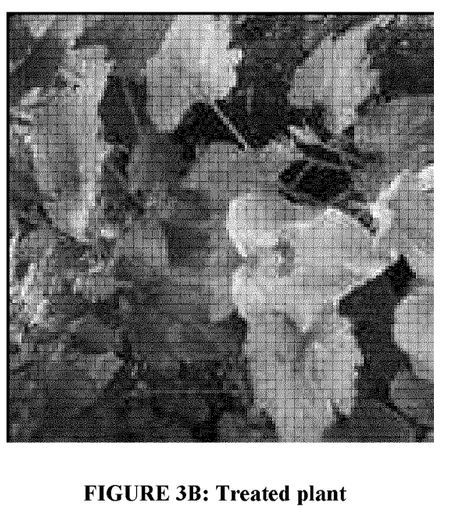

FIGS. 3A and 3B shows the results of a twice a day application over 3 days of a foliar spray comprising an aqueous 1:10 (1 part root to 10 parts water) extract of *Chelidonium majus* root with no surfactant.

As a result of this test, is noted plant's vigor and health are regained; plants flower and produced crop again. Fungi has first browned and then died. 14 days post last treatment one of the infected leaves is still alive with green zones. If the fungus infection had survived the leaf would have died and browned completely.

Figure 4A:
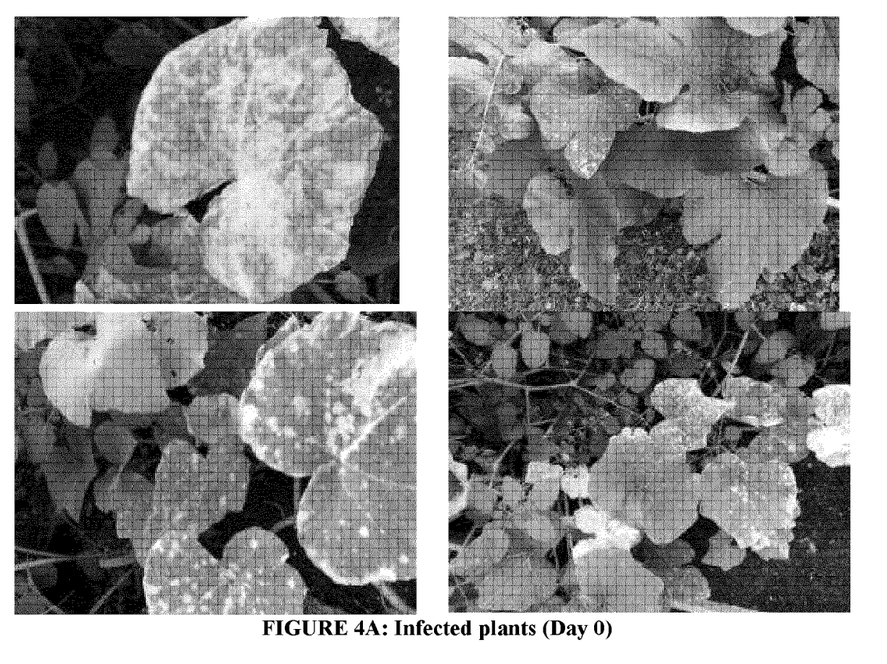
FIGS. 4A, 4B and 4C are pictures of cucurbits plants before treatment (FIG. 4A), one day after treatment (FIG. 4B) and two days after treatment (FIG. 4C), with a composition in accordance with another preferred embodiment.
Figure 4B:
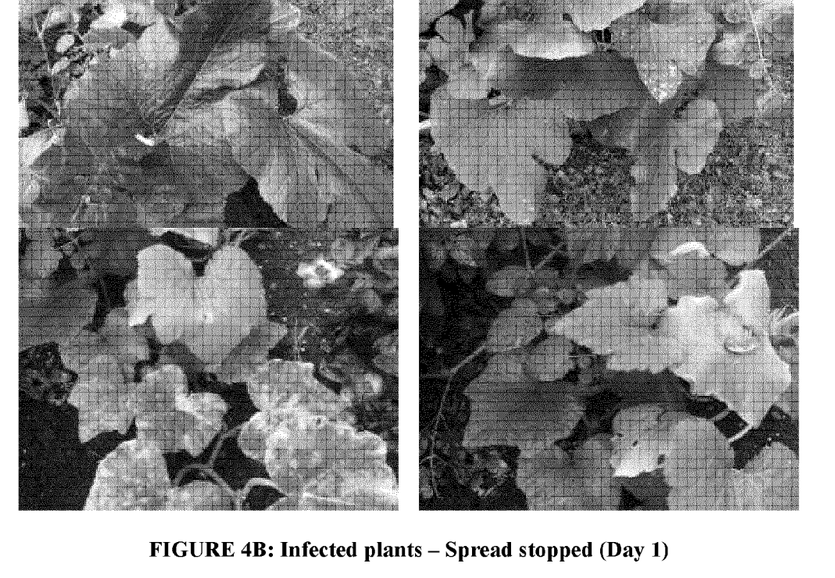
Figure 4C:
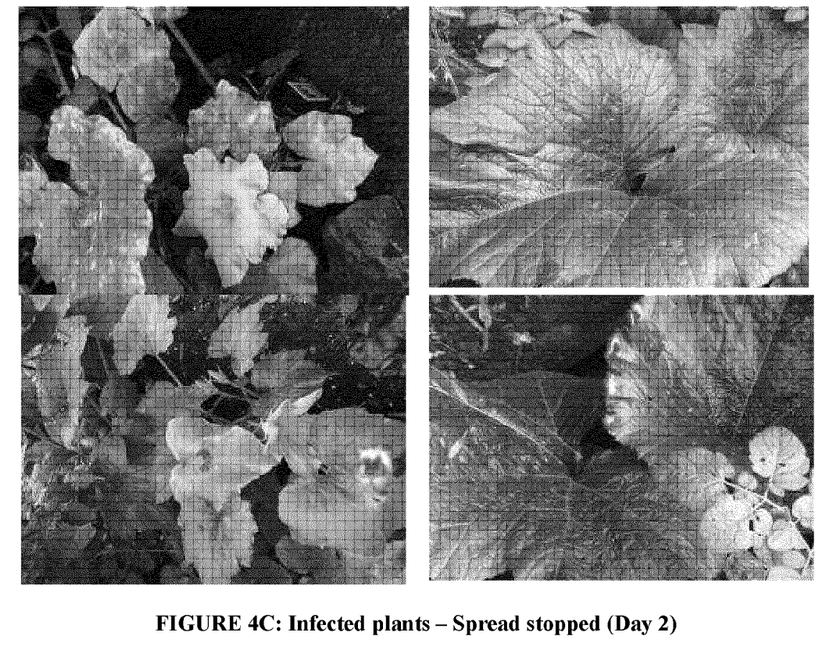

FIGS. 4A to 4C shows the results of a twice a day application over 3 days of a foliar spray comprising an aqueous 1:10 (1 part root to 10 parts water) extract of *Chelidonium majus* root with 0.25% of a surfactant (polysorbate 20).

As a result of this test, is noted plant's vigor and health are regained; plants flower and produced crop again with a nice shining green color of the leaves. Fungi has first browned and then died.

Example 4: Treatments of Cucurbits Infected with Mildew Fungus

A test using aqueous 1:10 (1 part root to 10 parts water) extract of *Chelidonium majus* root with 0.25% surfactant (polysorbate 20). in the treatment of Mildew infection of cucurbits. A single daily application has been performed over 3 days.

Figure 5:
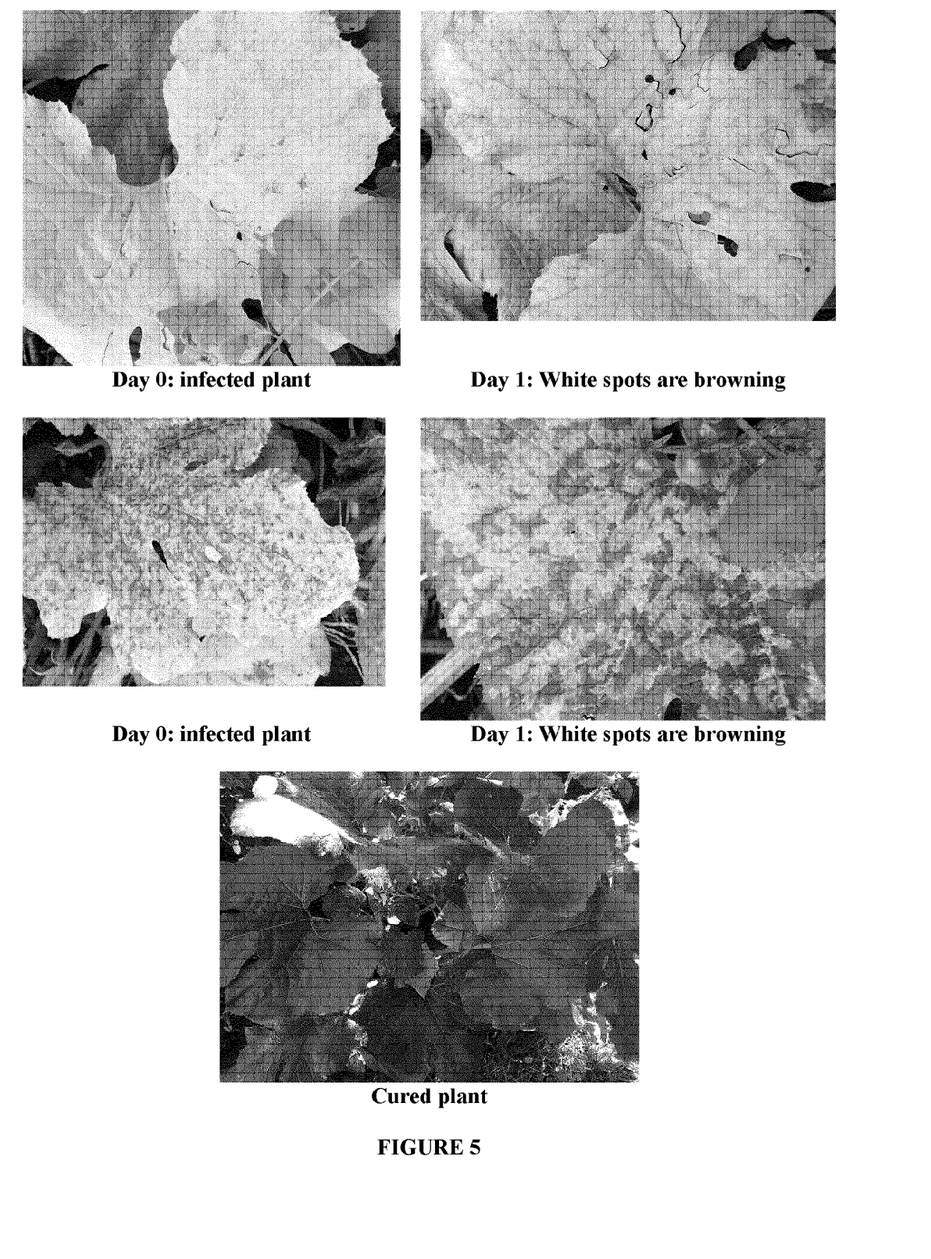
FIG. 5 comprises a plurality of pictures of cucurbits plants before treatment and after treatment with a composition in accordance with another preferred embodiment.

The pictures of FIG. 5 shows the efficacy of the treatment.

Example 5: English Cucumber

CELEXT07 is a proprietary botanical extract that can be used alone or in combination with algae fertilizers to help increase crop yield and stimulate plant growth.

The botanical agent can also be used to help prevent and treat fungal infections.

Field studies have shown that the botanical agent does not cause damage to plants during growth, flowering and fruit growth.

CELEXT07 is readily soluble in water at room temperature at 0.2%, 0.5% and 1% with or without the algae fertilizer at 6 ml per litre.

CELEXT07 increased crop growth in greenhouse grown English cucumber plants.

Plants were treated every 14 days with a solution containing Stimulagro™ with or without 0.5% of CELEXT07.

Figure 6A:
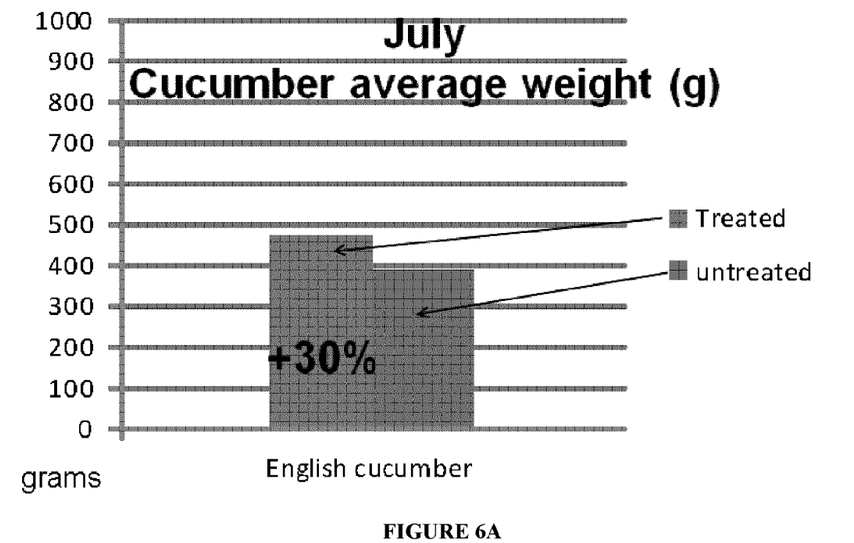
FIG. 6 are graphics and pictures regarding the treatment of English Cucumber.
Figure 6B:
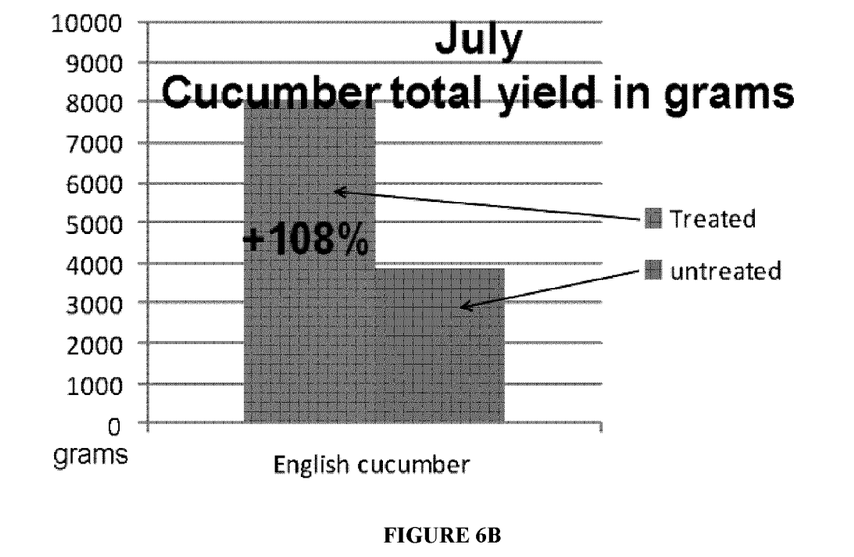
Figure 6C:
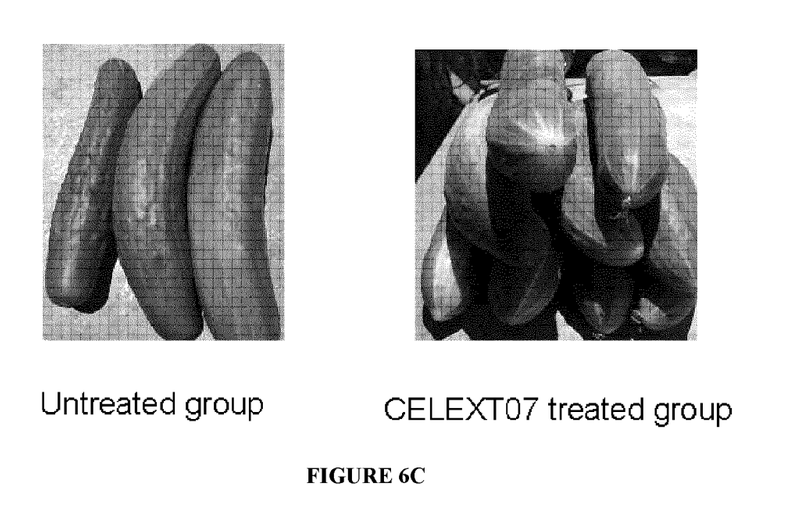

Results are presented on FIG. 6 and show a 30% increase of the cucumber weight and a 108% increase of total yields in grams with the treatment. Also, the cucumbers are visibly bigger.

Example 6: Increase of Crop Yield and Stimulation of Plant Growth

CELEXT07 was applied every two weeks in combination with an algae fertilizer on Ground Cherry.

Figure 7:
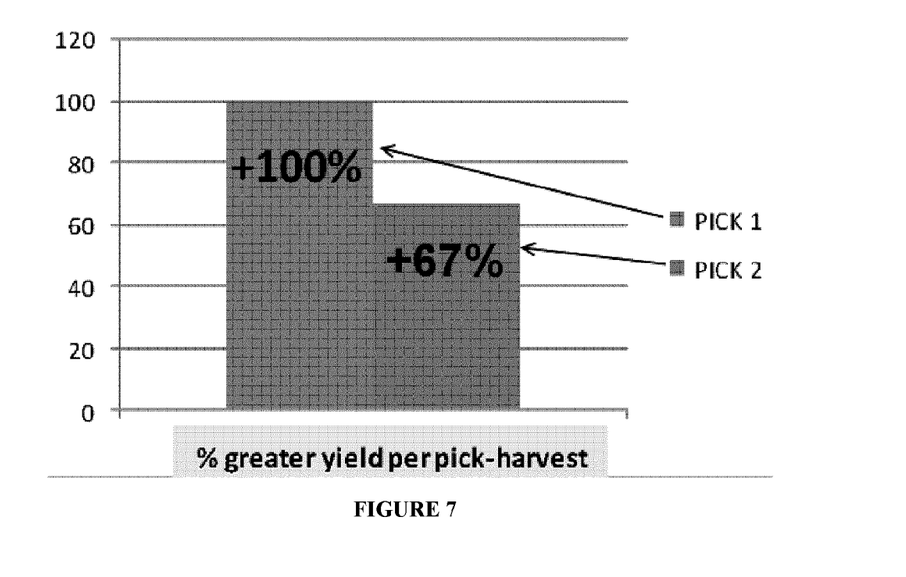
FIG. 7 is graphics showing the increase of crop yield on Ground Cherry.

As shown on FIG. 7, the addition of CELEXT07 to the base treatment resulted in a significant increase in crop yield compared to the base algae fertilizer treatment.

CELEXT07 was sprayed every two weeks onto the foliage of two year old marshmallow plants grown on a soil plot with a black colored plastic membrane.

The comparator groups consisted of two year old plants: control with no method to enhance growth; and a comparator group that used a black color plastic membrane over the soil surrounding the plants.

Figure 8:
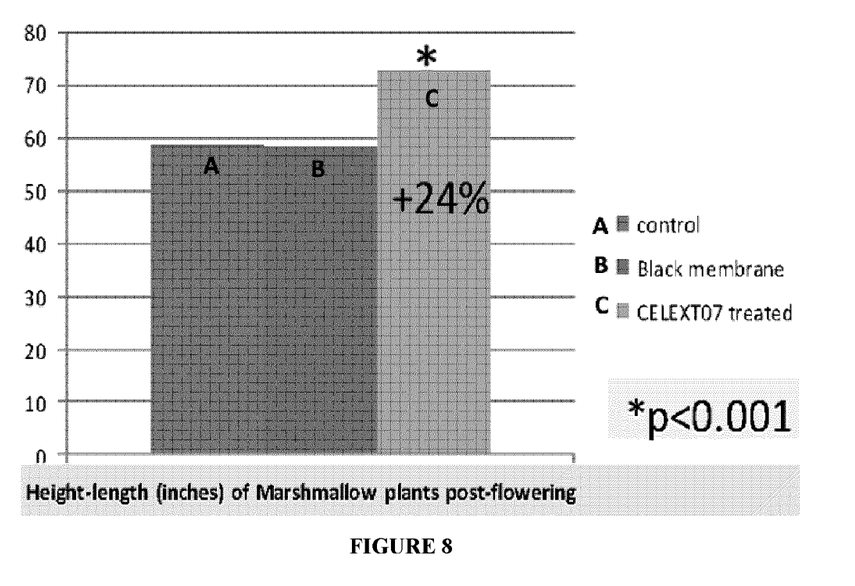
FIG. 8 is graphics showing the increase of crop yield on Marshmallow (Althea)
Figure 9:
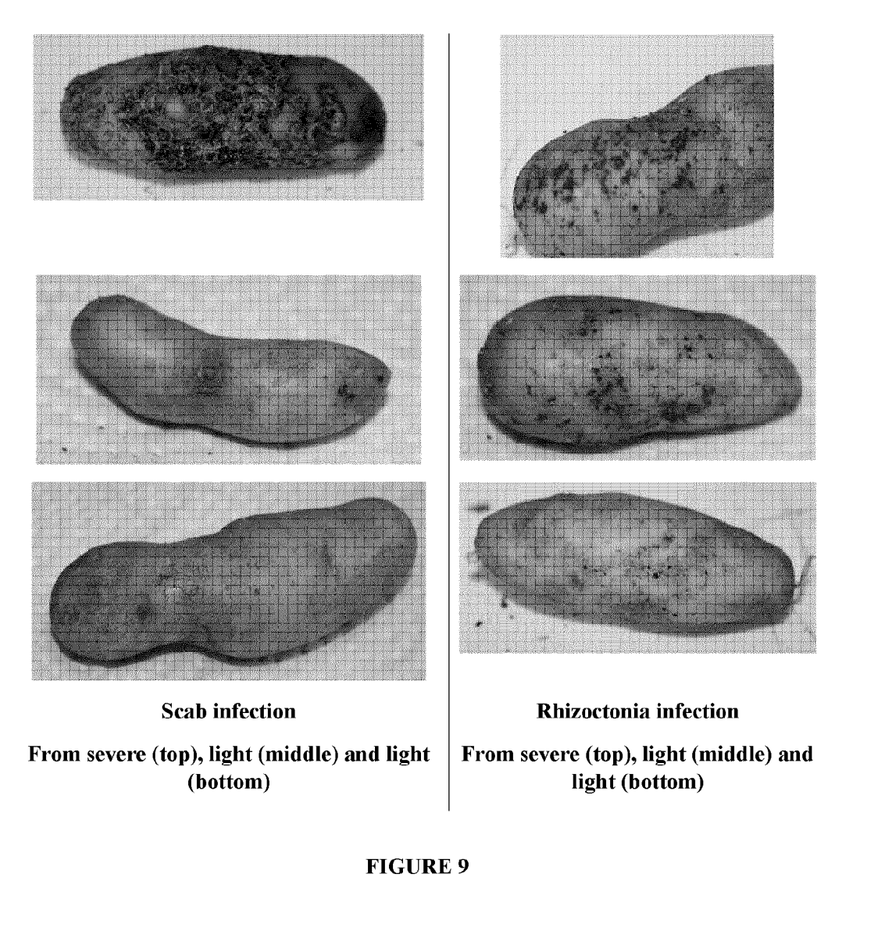
FIG. 9 are pictures showing the different stages of infections of a potato.

As shown on FIG. 8, CELEXT07 treated Marshmallow plants were statistically larger and longer than untreated plants; including those grown with a black colored plastic membrane. In addition, there was a 24% greater yield.

Example 7: Tolerability on all Crops, Ornamentals and Herbs

Several studies were performed to assess the safety and tolerability of the compositions according to the present invention.

One study involved the application of CELEXT07 in combination with an algae fertilizer every two weeks. The formulation was applied as a soil drench and sprayed onto the foliage, flowers and fruit of a variety of crops grown in a greenhouse environment in full sun.

The study began on May 24th and there are no signs of injury or suggestion of a negative effect on growth after 7 applications.

A second study was performed on crops, ornamentals and herbs growing outdoors. Plants were sprayed weekly with escalating doses of CELEXT07 and subsequently with CELEXT07 in combination with other antimicrobial herbal agents. The study also began on May 24th and to date there have been no signs of injury or toxicity. CELEXT07 was applied using a pressurized spray tank and tested at 0.5%, 1% and 2% CELEXT07. For each concentration, CELEXT07 was applied weekly for 3 or 5 consecutive weeks.

The combination study is still ongoing and the other agents are tested in combination with 1% CELEXT07. To date there are also no signs of toxicity or injury.

Example 8: Treatment of Intumescence (a Greenhouse Disease)

Intumescences is a physiological disease that affects plant growth in greenhouses. Intumescences are small, bump-like protrusions on the surface of leaves, petioles and stems of affected plants. Prevention of intumescences is important for crops or ornamental plants with an aesthetic value. Any reduction in aesthetic value can reduce salability as consumers may be hesitant to buy a plant that looks diseased or injured.

Aesthetics aside, intumescences can also dramatically alter physiological processes in the plant. As intumescences form across the leaf surface, photosynthetic activity may decrease as plants slowly lose leaf area available for this process.

Additionally, as intumescences form on the leaf veins and stems, water and nutrient transport may also be affected in the plant. In cases of severe intumescence development, gradual senescence of leaf tissue can occur.

Use of 0.5% CELEXT07 has prevented the development of Intumescences in greenhouse grown Ground Cherry fruit plants. Plants were treated every 14-days with a solution containing Stimulagro™ with or without 0.5% CELEXT07.

Groups:

| # | Treatments: |
|---|---|
| A | Algae fertilizer alone |
| B | Algae fertilizer plus 0.2% CELEXT07 and blend of polyphenols |
| C | Algae fertilizer plus 0.5% CELEXT07 and blend of polyphenols |
| D | Algae fertilizer plus 1% CELEXT07 and blend of polyphenols |
| E | Algae fertilizer plus 0.2% CELEXT07 |
| F | Algae fertilizer plus 0.5% CELEXT07 |
| G | Algae fertilizer plus 1% CELEXT07 |
| H | Sham (no algae fertilizer and no CELEXT076) |

Blend of polyphenols = 1 g/L of thymol (0.1%) plus 1 g/4 L of carvacrol (0.1%)

There are over 2400 potatoes that have been processed. The method used for scoring is given in "Potato Field Guide, Insects, Diseases and Defects, Publication 823, Eugenia Banks, 2004, Ministry of Agriculture and Food, Queens Printer for Ontario, Toronto, Ontario".

Dilute 60 ml of the algae preparation in 10 litres of water (6 ml per litre). Products tested for groups A to G contain the 6 mL per litre of algae fertilizer. Group H has is a sham control and does not receive any antifungal products and no algae fertilizer. The other groups contain ingredients as described in the table below.

Groups:

| # | Treatment | CELEXT07 | Thymol | Carvacrol |
|---|---|---|---|---|
| A | Algae fertilizer alone | 0 | 0 | 0 |
| B | Algae fertilizer plus 0.2% CELEXT07 and blend of polyphenols | 2 g/L or 8 g/4 L | 1 g/L or 4 g/4 L | 1 g/4 L |
| C | Algae fertilizer plus 0.5% CELEXT07 and blend of polyphenols | 5 g/L or 20 g/4 L | 1 g/L or 4 g/4 L | 1 g/4 L |
| D | Algae fertilizer plus 1% CELEXT07 and blend of polyphenols | 10 g/L or 40 g/4 L | 1 g/L or 4 g/4 L | 1 g/4 L |
| E | Algae fertilizer plus 0.2% CELEXT07 | 2 g/L or 8 g/4 L | 0 | 0 |
| F | Algae fertilizer plus 0.5% CELEXT07 | 5 g/L or 20 g/4 L | 0 | 0 |
| G | Algae fertilizer plus 1% CELEXT07 | 10 g/L or 40 g/4 L | 0 | 0 |
| H | Sham (no algae fertilizer and no CELEXT07) | 0 | 0 | 0 |

Example 9: Treatment of Potatoes and Potato Plants

Primary objective: The primary objective of this study is to demonstrate that a bimonthly application of the product prevent the development of fungal infections.

Secondary objective: The primary objective of this study is to demonstrate that the bimonthly application of the product does not damage the foliage or hinder growth, and also that the bimonthly application improve crop yield.

Description of Study Design: This study is a parallel group design comparing various antifungal formulations containing the algae-fertilizer with CELEXT07 with and without polyphenols (thymol and carvacrol). The products are applied bimonthly by soil application to drench the roots. Photos of plants treated in all groups were taken bimonthly. The weight and length of the daughter potatoes were taken at the end of the growth season as well as a count of the number of scab-like markings, and that from other microorganisms, on the potato.

Study Procedures—Bimonthly Treatment

Every 14 days, the solution is applied to the soil surrounding each plant. The plants in all groups were examined daily for signs of injury and photos were taken bimonthly. The weight and length of the daughter potatoes were taken at the end of the growth season.

The number of potatoes will be recorded for each of the following observations:

Signs of late blight;

Signs of scab

Signs of black scurf

No abnormal signs.

Compounds:

CELEXT07 is a 10:1 ethanol-water extract of the *Chelidonium majus* root. 10=amount of root; 1=amount of ethanol-water.

Results:
Powdery and Common Scab

| | GROUP | | | | | | |
|---|---|---|---|---|---|---|---|
| | A (%) | H (%) | B (%) | C (%) | D (%) | E (%) | F (%) | G (%) |
| T | 66 | 64 | 84 | 89 | 88.2 | 79.4 | 91.8 | 87.5 |
| L | 17 | 24 | 11 | 10 | 11.4 | 14.9 | 7 | 10.6 |
| TL | 9 | 7 | 4 | 0 | 0 | 0 | 0 | 0 |
| M | 4 | 3 | 1 | 0.4 | 0.4 | 4.4 | 0.4 | 1.5 |
| S | 4 | 2 | 0.3 | 1 | 0 | 1.4 | 0.4 | 0.3 |

T = trace; 0-1% coverage
L = light; 1-5% coverage
TL = Top Light; 1-5% coverage (focused on one side)
M = moderate; 5-10%
S = severe; more than 10%.

1. Groups A and H: Treatment with the algae fertilizer was comparable to sham. Approximately 65% of the potatoes were 'free' of scab.
2. Group E is 0.2% of CELEXT07 with algae fertilizer. The addition of 0.2% CELEXT07 resulted in 15% more scab 'free' potatoes. 0.5% CELEXT07 resulted in 90% scab 'free' potatoes which is 25% more scab free. No added benefit of going from 0.5% to 1% (Groups F and G).
3. Group B to D were the addition of CELEXT07 and two polyphenols. The polyphenols were at a fixed dose for all 3 groups; only the % CELEXT07 varied. We observe the same result as in #2: no difference between the 0.5% and 1% groups with about 90% scab free; so a 25% higher benefit. At 0.2% you observe a 20% benefit. At the higher incidents of scab (M and S), the combo with polyphenols appears to have been more potent.

*Rhizoctonia*:

| | GROUP | | | | | | |
|---|---|---|---|---|---|---|---|
| | A (%) | H (%) | B (%) | C (%) | D (%) | E (%) | F (%) | G (%) |
| T | 52 | 72 | 79 | 92 | 94.3 | 87.5 | 89.7 | 95.3 |
| L | 23 | 14 | 15 | 7 | 2.9 | 3.7 | 6.6 | 3.1 |
| TL | 14 | 13 | 5 | 0.4 | 2.9 | 7.4 | 3.7 | 1.2 |
| M | 8 | 1 | 0.6 | 0.7 | 0 | 1.4 | 0 | 0.3 |
| S | 2 | 0.5 | 0 | 0 | 0 | 0 | 0 | 0 |

T = trace; 0-1% coverage
L = light; 1-5% coverage
TL = Top Light; 1-5% coverage (focused on one side)
M = moderate; 5-10%
S = severe; more than 10%

4. The treatment with the algae fertilizer increased the number of infected potatoes by 20%.
5. Treatment with CELEXT07 in Groups E, F and G had a significant benefit. In this case, we observe a higher benefit at 1% of the extract than at 0.2%. Versus the sham, we observe a 15, 17 and 23% benefit. Versus the algae group, the benefit is even larger.
6. In the case of CELEXT07 with the polyphenols, we observe a similar benefit.

We are seeing a clear antifungal preventive and treatment effect of the formulation. The treatment shows that it can penetrate a wax cuticle just like in the case of a finger or toe nail.

With these examples of treatment of tomatoes, cucurbits and potatoes, antifungal properties of the composition according to the present invention has been demonstrated.

Nail Infection

According to a preferred embodiment, the pharmaceutical composition disclosed herein comprises a suspension of botanical essential oils in ethanol-water fluid extracts as a treatment of fungal and bacterial infections of nails. The pharmaceutical composition is preferably a topical formulation The pharmaceutical composition for the treatment of nail or skin fungal and bacterial infections, may comprise an alcoholic extract (30-70% $H_2O$:ethanol or methanol) of *Chelidonium majus* root. It is preferably combined with an alcoholic extract (30-70% $H_2O$:ethanol or methanol) of *Thuja occidentalis* leaf, and more preferably combined with from about 1 to 5% of each of the following essential oils *Eucalyptus citriodora*, Tea tree oil and *Thymus vulgaris* flower-leaf and optionally a film-forming surfactant.

The pharmaceutical composition may comprise herbal natural phenolic compounds such as, but not limited to, natural phenolic compounds are thymol, carvacrol, eugenol, crassinervic acid, aduncumene, hostmaniane, gaudichaudanic acid, or the like.

The following composition in accordance with a preferred embodiment of the invention has been tested on plants or on patients suffering of nail infection:

| Ingredients: | wt. % |
|---|---|
| *Chelidonium majus* root extract | 44.6 |
| *Thuja occidentalis* leaf extract | 44.6 |
| *Eucalyptus citriodora*, essential oil | 1.8 |
| Tea tree oil | 2.7 |
| *Thymus vulgaris* flower-leaf | 0.9 |
| Surfactant (Polysorbate 20) | 5.36 |

Method of Making: 500 mL Preparation of Human Nail Formula

Step 1:
Thuya extract: 260 gram foliage dried macerated in 3 times its volume in 50% ethanol-water for 72 hours; filtered and solution retained.

Step 2:
*Chelidonium majus* extract (CELEXT07): 50 grams of 10:1 extract dissolved in 500 mL Step 3: Combine
223 mL Thuya extract
223 mL CELEXT07 from step 2.
*Eucalyptus Citriodora* Essential Oil: 9 mL
Tea tree essential oil: 13.5 mL
*Thymus Vulgaris* (Thyme) Flower/Leaf Essential Oil: 5 mL
26.5 g of surfactant (polysorbate 20)

It is also disclosed a method for the making of the formulation as defined herein. The method comprises the step of macerating the plants in solvent for 24 to 72 hours.

The invention can be used as a topical solution or spray for application to the nail or skin: brush, metered dose device, patch, bandage or spray, thereby forming a film on the treated surface. The lipophilic nature of the oil-film coating remains on the nail or skin surface enabling the active molecules to penetrate the nail or skin for topical therapeutic use in the treatment of fungal nail, mucosal and cutaneous infections.

It is also disclosed a method for treating nail and/or skin infections, comprising the step of applying at least once a day the formulation as defined herein to a site of the body to be treated (nail or skin).

The method of application includes injecting locally above or adjacent to the nail's root a small volume of about 10 to 500 microliters of a drug depot formulation. The formulation may preferably contain between about 0.1 and 10 µg per µL of active ingredients.

The term "Drug depot" is hereby defined as injection of a liquid that remains at the site of injection (adjacent or above the nail root where injected) and slowly diffuses from the site over a period of several weeks. The liquid may remain a liquid at the site.

The drug depot formulation may consist of the natural phenolic compound alone as monotherapies, or in combination with other natural phenolic compounds, or in combination with synthetic antifungal or antibacterial drugs dissolved in a vehicle base that is biocompatible with tissues.

The vehicle that is biocompatible with tissues can be:
A sustained-release drug depot formulation to extend the release of the composition. Sustained-release includes: formulation technologies such as microparticles, microspheres and nanospheres, traditional depots, and injectable implants;
Suspension,
Sesame oil solution,
Vegetable oil solution,
Cottonseed oil solution, or
Polymer implant.
Vehicle-Base Formulations for Local Injection:
Oil-based injectable solutions, injectable-drug suspensions, polymer-based microspheres (PLGA microspheres, PCL microspheres, polyanhydride microspheres, polyorthoesters microspheres, and polyalkylcyanoacrylate microspheres) and polymer-based in-situ forming. Formation of microspheres includes use of homopolymers and copolymers of lactic acid and glycolic acid (PLGA). Microparticles prepared using lipids to encapsulate the antifungal/antibacterial composition include Liposomes composed of a single or multiple phospholipids and cholesterol bilayers.
Alternatively, a conventional long-acting injection formulation that consists either of lipophilic compounds in aqueous solvents as suspensions or of lipophilic compounds dissolved in vegetable oils.
Conventional biodegradable polymers used for controlled drug delivery can be used: includes polylactides (PLA), polyglycolides (PGA), poly(lactide-co-glycolide) (PLGA), poly(ε-caprolactone) (PCL), polyglyconate, polyanhydrides, polyorthoesters, poly(Dioxanone), and polyalkylcyanoacrylates.

The patients used the product to treat an active infection of the toe nail. The product was applied once in the morning. After several 12 weeks of treatment, the infected zone of the nail began to darken and eventually became dark brown and the patients began to observe new growth that was not infected. As the new nail grew, the dark zone was removed by frequent cutting.

While illustrative and presently preferred embodiments of the invention have been described in detail hereinabove, it is to be understood that the inventive concepts may be otherwise variously embodied and employed and that the appended claims are intended to be construed to include such variations except insofar as limited by the prior art.

What is claimed is:

1. A phytosanitary composition comprising:
between 0.2 and 2 wt % of *Chelidonium majus* root aqueous extract; and
between 0.1 to 5 wt % of at least one natural phenolic compound;
wherein the composition is usable for prevention or treatment of plant infections.

2. The phytosanitary composition of claim 1, wherein the at least one natural phenolic compound comprises phenolic acids, thymol, carvacrol, eugenol, crassinervic acid, aduncumene, hostmaniane, gaudichaudanic acid, flavonoids, tannins, stilbenes, curcuminois, coumarins, ligans, quinines, or mixture thereof.

3. The phytosanitary composition of claim 2, further comprising from 0.1 to 1 wt. % of an aqueous extract of *Thuja occidentalis* leaf.

4. The phytosanitary composition of claim 1, further comprising an additive selected from the group consisting of penetrants, thickeners, emulsifiers, spreader, stickers, crop oils, inorganic oils, alkyl polyglucosides, and organosilicate surfactants.

5. The phytosanitary composition of claim 1, further comprising an antifungal compound.

6. The phytosanitary composition of claim 5, wherein the antifungal compound is selected from the group consisting of amphotericin B, terbinafine, tavaborole, ciclopirox, griseofulvin, an azole antifungal, an echinocandins, and flucytosine.

7. The phytosanitary composition of claim 6, wherein the azole antifungal is ketoconazole, fluconazole, itraconazole, posaconazole, voriconazole, or efinaconazole; and the echinocandin is anidulafungin, caspofungin, or micafungin.

8. The phytosanitary composition of claim 1, further comprising an antibacterial compound.

9. The phytosanitary composition of claim 8, wherein the antibacterial compound comprises beta-lactam antibiotics, macrolide antibiotics, lincosamides, streptogramins, aminoglycosides, quinolones, sulfonamides, tetracyclines, chloramphenicol, metronidazole, tinidazole, nitrofurantoin, glycopeptides, lipoglycopeptides, oxazolidinones, rifamycins, polypeptides and tuberactinomycins or mixtures thereof.

10. The phytosanitary composition of claim 1, wherein the aqueous extract of *Chelidonium majus* root is a 10:1 ethanol-water extract of the *Chelidonium majus* root, with 10 being the amount of *Chelidonium majus* root and 1 being the amount of ethanol-water.

11. The phytosanitary composition of claim 1, being used for stimulating plant growth or increasing crop yield.

12. The phytosanitary composition of claim 1, the phytosanitary composition further comprising between 0.1 to 0.25 wt. % of film-forming surfactant.

13. The phytosanitary composition of claim 12, wherein the film-forming surfactant comprises a polysorbate-type nonionic surfactant.

14. The phytosanitary composition of claim 1, the at least one natural phenolic compound comprising between 0.1 to 0.5 wt % of thymol.

15. The phytosanitary composition of claim 14, the phytosanitary composition further comprising between 0.1 to 0.5 wt. % of Carvacrol.

16. The phytosanitary composition of claim 15, the phytosanitary composition further comprising between 0.1 to 1 wt. % of *Thuja occidentalis* leaf aqueous extract.

17. The phytosanitary composition of claim 11, the composition stimulating plant growth or increasing crop yield of one or more of the followings: English cucumber, marshmallow and ground cherry.

18. The phytosanitary composition of claim 1, the composition being used to prevent or treat one or more of the selected plant infections: tomato blight, tomato powdery mildew, cucurbits mildew fungus and potatoes common scab.

19. The phytosanitary composition of claim 14, the composition further comprising at least one natural aromatic compound.

20. The phytosanitary composition of claim 19, the natural aromatic compound being any one of the followings: protopine, stylopine, dihydrosanguinarine, and mixture thereof.

21. A phytosanitary composition for treating plant infection, comprising:
- from 0.2 to 1 wt. % of *Chelidonium majus* root aqueous extract;
- from 0.1 to 1 wt. % of *Thuja occidentalis* leaf aqueous extract;
- from 0.1 to 0.5 wt. % of Thymol;
- from 0.1 to 0.5 wt. % of Carvacrol; and
- from 0.1 to 0.25 wt. % of film-forming surfactant.

22. A phytosanitary composition for stimulating plant growth or increasing crop yield, comprising:
- from 0.2 to 1 wt. % of *Chelidonium majus* root aqueous extract;
- from 0.1 to 1 wt. % of *Thuja occidentalis* leaf aqueous extract;
- from 0.1 to 0.5 wt. % of Thymol;
- from 0.1 to 0.5 wt. % of Carvacrol; and
- from 0.1 to 0.25 wt. % of film-forming surfactant.

23. A method for the prevention and treatment of plant bacterial and fungus infections, comprising the step of applying at least once, the phytosanitary composition as defined in claim 1 on the plant, and letting the phytosanitary composition to dry to form a film on the plant.

* * * * *